(12) United States Patent
De et al.

(10) Patent No.: US 9,793,090 B2
(45) Date of Patent: Oct. 17, 2017

(54) E-BEAM INSPECTION APPARATUS AND METHOD OF USING THE SAME ON VARIOUS INTEGRATED CIRCUIT CHIPS

(71) Applicant: PDF Solutions, Inc., San Jose, CA (US)

(72) Inventors: Indranil De, San Jose, CA (US); Christopher Hess, Belmont, CA (US); Dennis J. Ciplickas, San Jose, CA (US)

(73) Assignee: PDF Solutions, Inc., San Jose, CA (US)

( * ) Notice: Subject to any disclaimer, the term of this patent is extended or adjusted under 35 U.S.C. 154(b) by 0 days.

(21) Appl. No.: 14/989,729

(22) Filed: Jan. 6, 2016

(65) Prior Publication Data

US 2016/0118217 A1    Apr. 28, 2016

Related U.S. Application Data

(63) Continuation of application No. 14/612,841, filed on Feb. 3, 2015, and a continuation of application No. 14/303,578, filed on Jun. 12, 2014, now abandoned, which is a continuation-in-part of application No. 14/190,040, filed on Feb. 25, 2014, now abandoned, which is a continuation-in-part of application No. 14/038,799, filed on Sep. 27, 2013, now abandoned.

(60) Provisional application No. 61/942,163, filed on Feb. 20, 2014, provisional application No. 61/971,306, filed on Mar. 27, 2014, provisional application No. 61/972,787, filed on Mar. 31, 2014, provisional application No. 61/982,652, filed on Apr. 22, 2014, (Continued)

(51) Int. Cl.
*H01L 23/58* (2006.01)
*H01J 37/22* (2006.01)
*G01R 31/26* (2014.01)
*H01L 21/66* (2006.01)
*H01J 37/147* (2006.01)
*H01J 37/20* (2006.01)
*H01J 37/285* (2006.01)
*G01N 23/225* (2006.01)

(52) U.S. Cl.
CPC ............ *H01J 37/222* (2013.01); *G01R 31/26* (2013.01); *H01J 37/147* (2013.01); *H01J 37/20* (2013.01); *H01J 37/285* (2013.01); *H01L 22/12* (2013.01); *H01L 22/20* (2013.01); *H01L 22/30* (2013.01); *G01N 23/2251* (2013.01); *G01R 31/2644* (2013.01); *H01J 2237/24592* (2013.01)

(58) Field of Classification Search
USPC ............ 257/48; 250/310, 311, 492.1, 492.2, 250/492.3; 324/751; 382/103, 145, 153
See application file for complete search history.

(56) References Cited

U.S. PATENT DOCUMENTS 7,635,843 B1 * 12/2009 Luo .................. H01L 22/12
250/307
2005/0121611 A1 * 6/2005 Kimba ................ G01N 23/225
250/311

* cited by examiner

*Primary Examiner* — Timor Karimy
(74) *Attorney, Agent, or Firm* — Pillsbury Winthrop Shaw Pittman LLP

(57) ABSTRACT

The present invention discloses an e-beam inspection tool, and an apparatus for detecting defects. In one aspect is described an apparatus for detecting defects that includes a focusing column that accelerates the e-beam and separately, for each of the plurality of predetermined locations, focuses the e-beam to a predetermined non-circular spot that is within the predetermined surface area of each of the plurality of predetermined locations based upon the major axis.

21 Claims, 24 Drawing Sheets

Related U.S. Application Data provisional application No. 62/011,161, filed on Jun. 12, 2014.

E-BEAM INSPECTION APPARATUS AND METHOD OF USING THE SAME ON VARIOUS INTEGRATED CIRCUIT CHIPS

CROSS-REFERENCE TO RELATED APPLICATIONS

This application is a continuation of U.S. patent application Ser. No. 14/612,841 filed Feb. 3, 2015, which claims priority to Provisional U.S. Patent Applications: Ser. No. 61/942,163 filed Feb. 20, 2014; Ser. No. 61/971,306 filed Mar. 27, 2014; Ser. No. 61/972,787 filed Mar. 31, 2014; Ser. No. 61/982,652 filed Apr. 22, 2014; Ser. No. 62/011,161 filed Jun. 12, 2014; and which '841 application is a continuation of U.S. patent application Ser. No. 14/303,578 filed Jun. 12, 2014, which is a continuation-in-part of U.S. patent application Ser. No. 14/190,040, filed Feb. 25, 2014, which is a continuation-in-part of U.S. patent application Ser. No. 14/038,799, filed Sep. 27, 2013. All applications are incorporated by reference herein.

FIELD OF THE INVENTION

This invention relates to the field of semiconductor integrated circuits and to methods for manufacturing and testing such circuits.

BACKGROUND OF THE INVENTION

A "charged particle column" is used to direct a beam of finely focused charged particles on any sample surface. Such columns are used in tools to irradiate various types of specimen for the purposes of a variety of applications. The following examples relate to columns built for "electrons" but similarly apply to other "columns" that are used to irradiate charged atoms also knows as "ions".

Scanning electron microscopes ("SEM") are used gather images of specimens at high magnifications. The beam rasters across a certain area and captures an image. A specific type of SEM, known as a high resolution scanning electron microscopes gather images at very high resolution and low beam current and used to measure dimensions of features on the image, whereas a review scanning electron microscope is used to obtain images at specific locations on the surface of semiconductor wafer used for fabricating integrated circuits already identified by another tool as defects/local abnormalities for the purposes of taking high-resolution images of the defects.

Another type of charged particle tool, known as an e-beam defect inspection tool, is used for localizing "defects" i.e. local abnormalities on the surface of semiconductor wafer used for fabricating integrated circuits.

Another type of charged particle tool, known as an e-beam writer, makes specific patterns on a photoresist layer that has been coated on a semiconductor wafer or a photolithography mask for the purpose patterning these shapes onto an underlying later.

Still another type of charged particle tool, known as an e-beam spectroscopy tool, uses a focused electrical beam to study local properties on sample surface by exciting the sample surface and generating secondary particles whose characteristics are measured in some way e.g. electrons in Auger spectroscopy or Xrays-photons in Energy Dispersive Spectroscopy, etc.

Since the embodiments described herein are for a defect inspection tool, a further background of conventional defect inspection tools is provided. E-beam defect inspection tools are used in two modes. In a first mode, physical defect inspection, the electron beam gathers images of large enough areas to be able to capture a physical defect or abnormality of interest i.e. the defect physically appears in the area being imaged and is visible in the image created in the detector. Note that the defect need not be. "clearly" visible for the inspection tool to operate. It must only generate a signal strong enough to suggest that a defect exists. Once the inspector has localized the defect it is typically used to gather higher resolution images in a Review SEM, as mentioned above. In a second mode, voltage contrast inspection, changes in potential at the wafer surface are detected. The change in wafer potential may happen as a result of a "physical defect" such as a particle or a purely electrical defect such as a dislocation in a crystal causing higher electrical leakage. In either case the ebeam defect inspection tool is sensing the voltage change at specific location on the semiconductor wafer as the proxy for the defect itself. The voltage change resulting from the defect typical requires some type of an excitation of the circuit underneath. This can happen as a result of the ebeam that is being used to sense the voltage contrast itself (also known as passive voltage contrast) or application of a separate electrical bias on the semiconductor wafer (also known as active voltage contrast).

One example of a conventional active voltage contrast e-beam inspection tool is provided by U.S. Pat. No. 7,679,083 B2 ("Semiconductor integrated test structures for electron beam inspection of semiconductor wafers") to S. Jansen, et al. The '083 patent describes conventional electron beam inspection, using an electron beam that irradiates the target region, thus causing the emission of secondary electrons and a secondary electron detector measures the intensity of the secondary electron emission along the scan path of the electron beam. As a region is scanned, electrons from the electron beam induce surface voltages that vary over the scanned region due to differential charge accumulation of the irradiated features. Voltage contrast inspection operates on the principle that differences in the induced surface voltages over a scanned region will cause differences in secondary electron emission intensities.

As taught, in general, for a given feature, the intensity of secondary electron emission will vary depending on, e.g., the landing energy of the beam electrons (primary electrons) and material composition of the feature. For a given material, a secondary electron yield is a measure of a ratio of secondary electron emission to impinging primary electrons as a function of landing energy (eV). Different materials irradiated by an electron beams tuned to a specific landing energy will emit different intensities of secondary electrons. The different features within the scanned target region will be displayed in an SEM image with different grayscale shades depending on the intensity of secondary electron emission. The irradiated features having a higher intensity of secondary electron emission may be displayed brighter in an SEM image than those irradiated features having a lower intensity of secondary electron emission.

E-beam inspection tools operate by taking "images" of the semiconductor wafer at high enough resolution. The images are 20 images gathered in the areas where the defect must be localized (also known as a "care area") one of two ways. This is also illustrated in FIG. 1. Each point of the 20 image is referred to as a pixel.

1. "Step and scan": The wafer is held stationary to capture an image of the wafer at one location. The process is repeated until the whole care area is covered.

2. "Swathing". The wafer is moving when the image is being captured so that a whole strip of 2-D image is created also known as a swath. The process is repeated with multiple swaths until the whole care area has been covered One common theme in both the above methods is that the care areas are sampled as full 20 images. The dwell time at each pixel is held constant at each pixel when gathering the image. Once an e-beam inspection tool has gathered an image of the care areas, it must find the defect. This is conventionally done is one of the following ways:

Array mode detection: Here the image is gathered in an area which has a repeating pattern such as a SRAM memory block. With the image, images of the neighboring memory blocks are compared and differences are flagged as a defect.

Random mode detection: Here images that have been gathered from identical dies of the wafer are compared to each other and differences are flagged as a defect. Note that the dies do need a repeating pattern inside as is required for array more inspection.

Die-to data base inspection: Here the images gathered are compared to a preexisting image saved on the computer and differences are flagged as a defect. The preexisting image may be created artificially from simulation of the inspected areas or from an image of a "golden die" that has been measured prior.

While a conventional e-beam inspection tool produces useful results, they are still less than ideal.

SUMMARY OF THE INVENTION

The present invention discloses several techniques for improving e-beam inspection and improving a scanning electron microscope.

An aspect of this invention relates to the use of a tool using a charged particle column (electrons or ions), whose primary function is to find defects on the surface of semiconductor wafers (i.e., function as an inspector). (While the present description uses the term "e-beam," it is understood that it applies to all charged beams, both electrons or ions, with electron being used herein to refer to both.)

According to an embodiment, there is described an apparatus for detecting defects in an integrated circuit, wherein the integrated circuit includes a plurality of predetermined locations each having a predetermined surface area and a major axis and the apparatus comprising:

a target holder for holding said integrated circuit; an e-beam source that directs an e-beam toward each of the plurality of predetermined locations on the integrated circuit;

a focusing column that accelerates the e-beam and separately, for each of the plurality of predetermined locations, focuses the e-beam to a predetermined narrow non-circular spot that is within the predetermined surface area of each of the plurality of predetermined locations based upon the major axis, the focusing column including a condensor lens, an objective lens and a Wehnelt; and a detector that detects a voltage contrast image of the secondary electrons emitted from the integrated circuit after the e-beam strikes each of the plurality of predetermined locations of the integrated circuit.

In accordance with one aspect of the invention, a computer into which is input the image and which determines whether a defect exists within the integrated circuit based upon the voltage contrast image, thereby forming an inspection tool.

In one embodiment of the apparatus for detecting defects in an integrated circuit is provided, the apparatus provides for e-beam inspection of a product IC wafer that includes an area of functional product circuitry, with a multiplicity of e-beam exercisable test structures (or pads/targets) distributed within the area of functional product circuitry; and, a plurality of e-beam skip zones, each of which allows an e-beam inspection tool to skip at least 10%, 15%, or 20% of its overall scan length (measured in the scan direction) without missing the opportunity to exercise any test structures (or pads/targets). Such product IC wafers may preferably further include at least: one or more empty e-beam scanning tracks, each spanning the entire width of the area of functional product circuitry, which the e-beam inspection tool can then also skip.

In one embodiment, the size of the beam on the wafer is not fixed, but is changed dynamically for each location being read out. The sizing of the spot on a per structure basis allows the beam to be optimized with respect to each structure. The optimization is typically to maximize the signal-to-noise ratio of the inspection.

Another aspect of the invention relates to design of a voltage-contrast device-under-test ("VC DUT"), with a test pad, where the complete structure is tested with very few pixels (<10). Such a VC DUT may have a test pad whose size and shape accommodates non-circular incident e-beams, while maximizing SNR at the same time. Such beams may also be square shaped to match pads that are similarly square shaped. Such pads may be configured to capture beams with an asymmetric aspect ratio (X/Y length ratio) that is greater than 3 (e.g., DUT with an X-dimension of 100 nm and Y dimension 300-600 nm would have aspect ratio of 3:1, 4:1, 5:1).

BRIEF DESCRIPTION OF THE DRAWINGS

These, as well as other, aspects, features and advantages of the present invention are exemplified in the following set of drawings, in which.

DESCRIPTION OF ILLUSTRATIVE EMBODIMENTS

Figure 1:
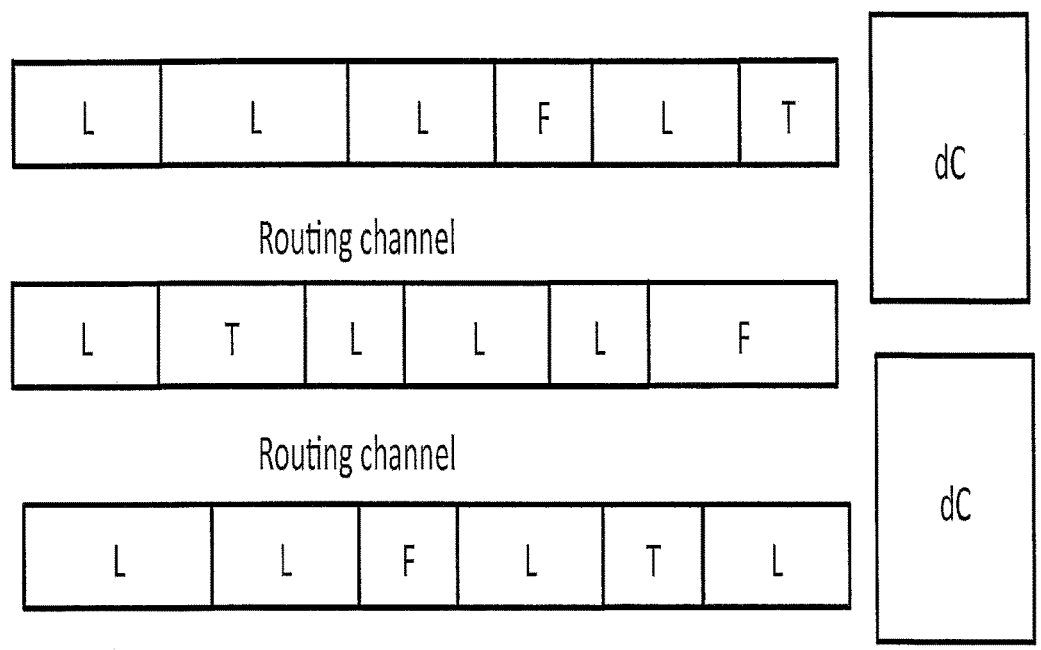
FIG. 1 conceptually depicts an illustrative section of a standard cell layout that includes logic cells (L), filler cells (F), and tap cells (T) arranged in rows, with routing areas between the rows, and nearby decap cells (dC)

FIG. 1 conceptually depicts an illustrative section of a prior-art standard cell layout that includes logic cells (L), tap cells (T) and filler cells (F) arranged in rows, with routing channels between the rows, and nearby decap cells (dC). As depicted, the overall distribution of decap, tap and filler cells within this illustrative section is irregular and does not follow any obvious pattern or symmetry. (Persons skilled in the art will immediately recognize that the depictions herein are conceptual, and only intended to illustrate the principles of the invention, rather than represent actual layout realities. Indeed, such skilled artisans will appreciate that tap cells typically come in only one size and appear at regular or nearly regular intervals. Similarly, such skilled artisans will also recognize that decap cells can, and frequently are, sized to fit within and placed within the standard cell rows.)

Figure 2:
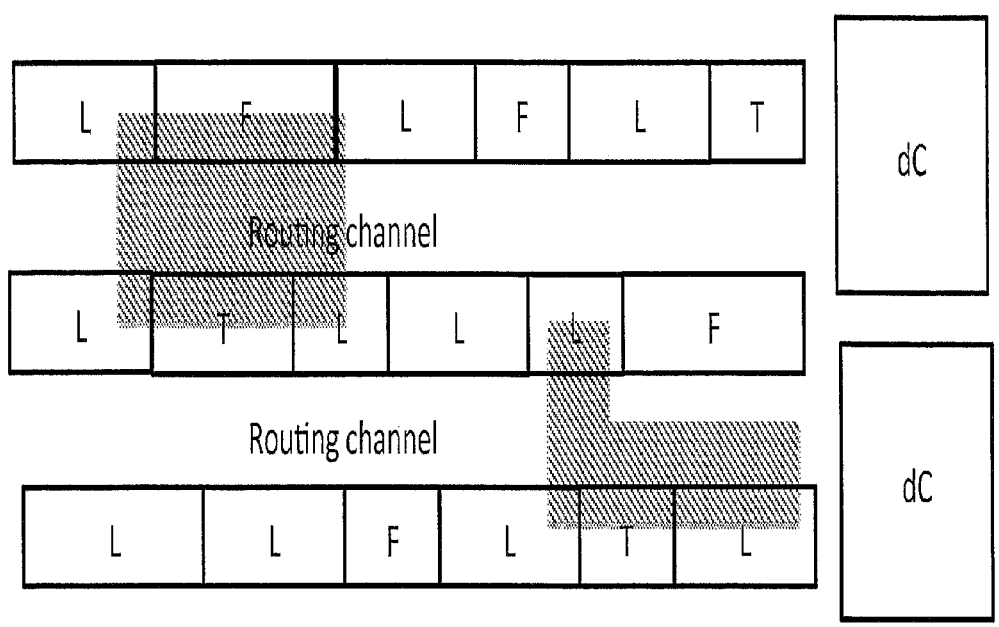
FIG. 2 depicts the same layout as FIG. 1, but with dummy fill areas indicated in a first layer.

FIG. 2 conceptually depicts the same prior-art layout as FIG. 1, but with dummy fill areas indicated in a first layer. These dummy fill areas are shown as diagonally hashed areas, and, as depicted, may be regularly (e.g., rectangular) or irregularly shaped. Dummy fill areas most useful in accordance with the invention typically appear on the third and above metal layers (e.g., M3, M4, M5, M6), but may also appear on lower metal and/or previous layers such as active, poly layer(s), or local interconnect. (As persons skilled in the art will appreciate, the depiction of dummy fill in FIG. 2 is conceptual, since dummy fill areas would typically be much larger in area than one or a few standard cells.)

Figure 3:
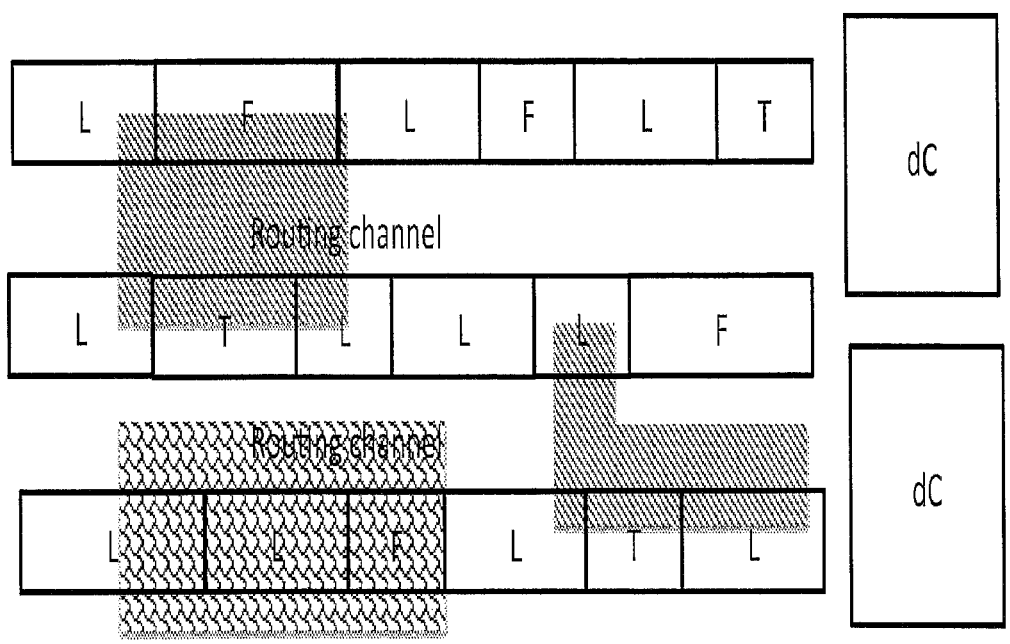
FIG. 3 depicts the same layout as FIGS. 1-2, but with dummy fill area(s) indicated in a second layer.

FIG. 3 conceptually depicts the same layout as FIGS. 1-2, but with dummy fill area(s) indicated in a second layer. This second-layer dummy fill area is shown in the scale pattern hashing.

Figure 4:
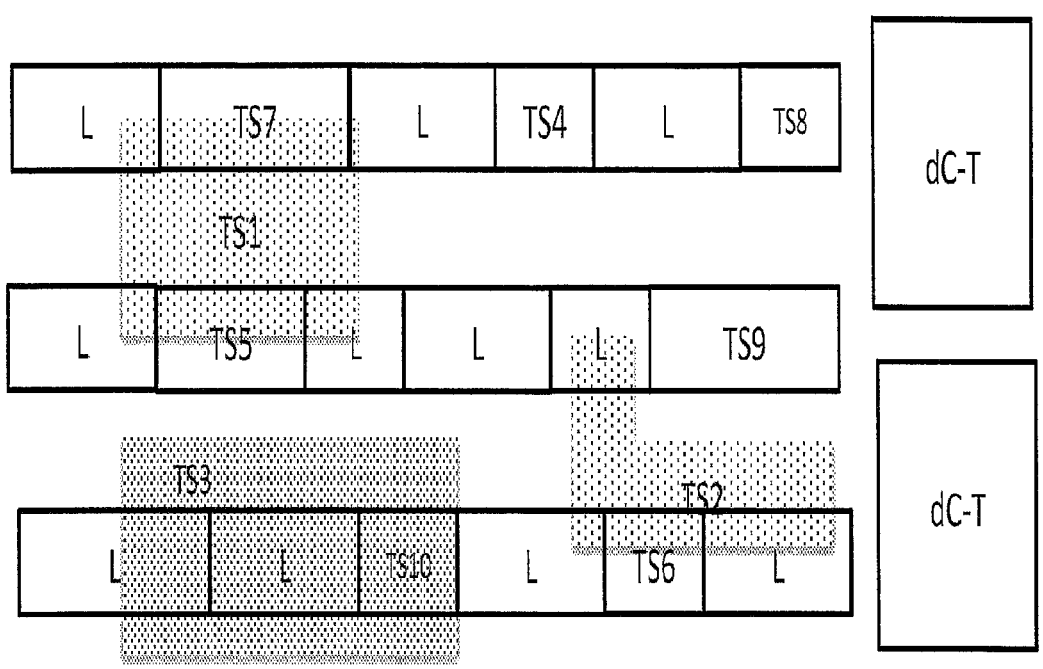
FIG. 4 depicts an exemplary layout in accordance with the invention, in which the filler cells, tap cells, decap cells, and dummy fill regions of the FIG. 3 layout are replaced by self-contained test structures.

FIG. 4 conceptually depicts an exemplary layout, based on that of FIG. 3, that illustrates certain aspects of the present invention. As exemplified in FIG. 4, filler cells (F) and tap cells (T) have been replaced by test structures (TS4, TS5, TS6, TS7, TS8, TS9, TS10), decap cells (dC) have been replaced by test-enabled decap cells (dC-T), and dummy fill regions have been replaced by test structures (TS1, TS2, TS3).

Figure 5:
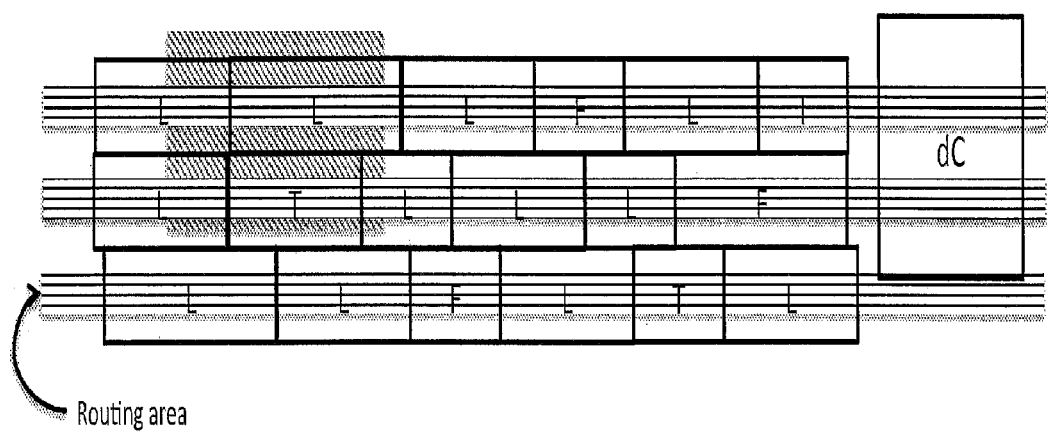
FIG. 5 conceptually depicts a preferred form of standard cell layout (for use in accordance with the invention)

FIG. 5 conceptually depicts a preferred form of standard cell layout, suitable for use in accordance with the invention. This figure depicts the more modern style, in which cell rows are abutting and routing areas are over-the-cells. Though not depicted, it should be understood that routing areas need not be regularly shaped, nor need they be oriented in a direction parallel to the rows.

Figure 6:
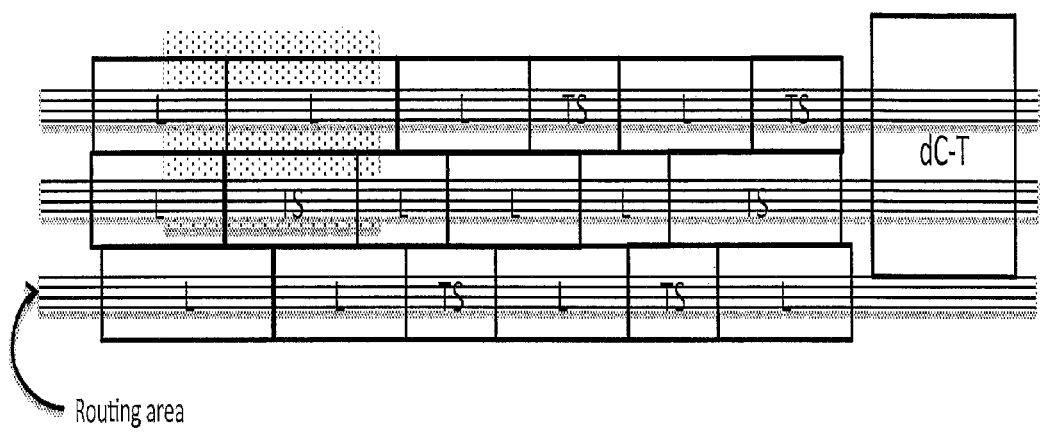
FIG. 6 depicts an exemplary layout in accordance with the invention, in which the filler cells, decap cells, tap cells, and dummy fill regions of the FIG. 5 layout are replaced by self-contained test structures.
Figure 7:
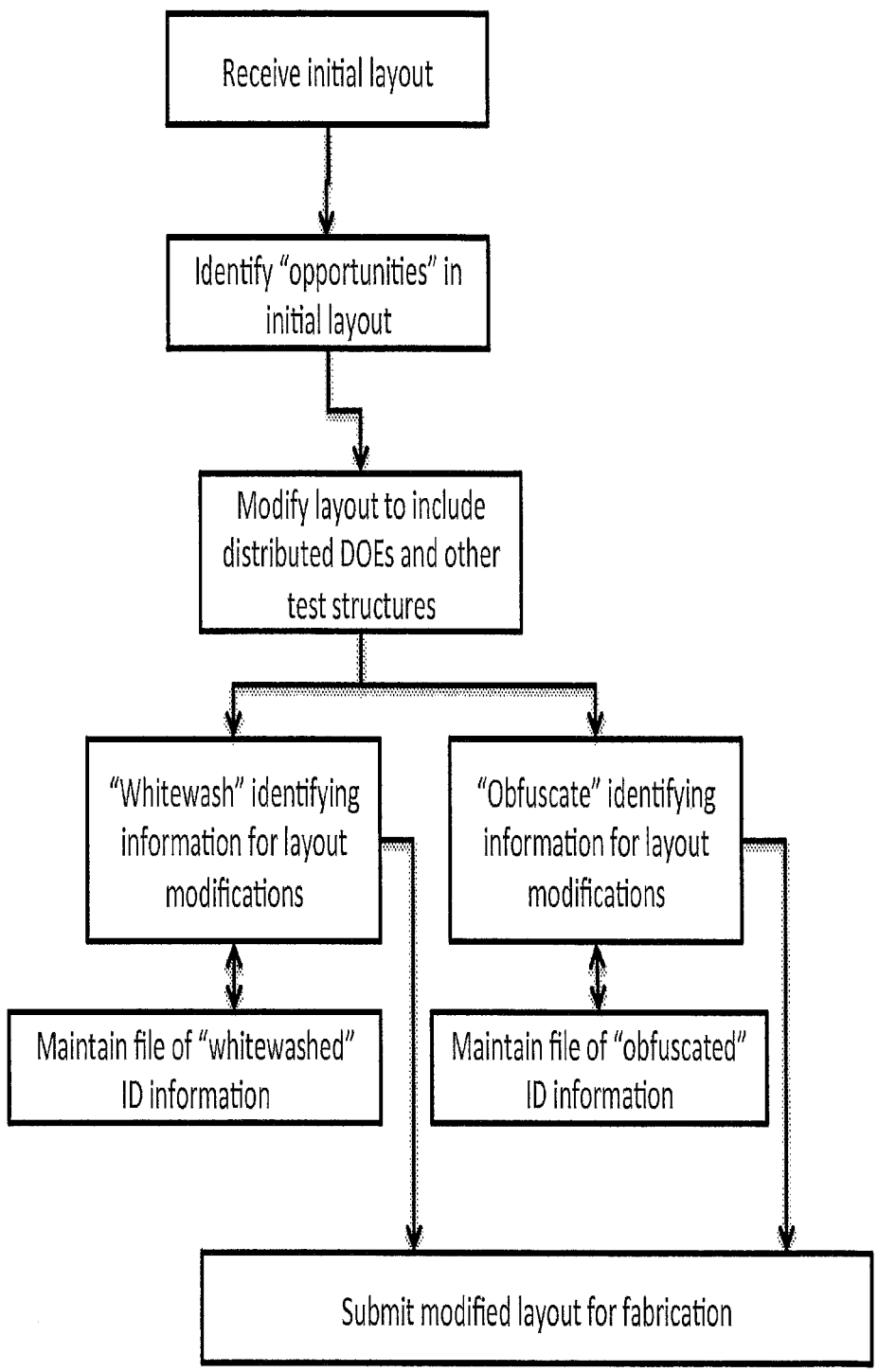
FIG. 7 depicts an exemplary process flow for opportunistic test structure insertion in accordance with certain embodiments of the invention.
Figure 8:
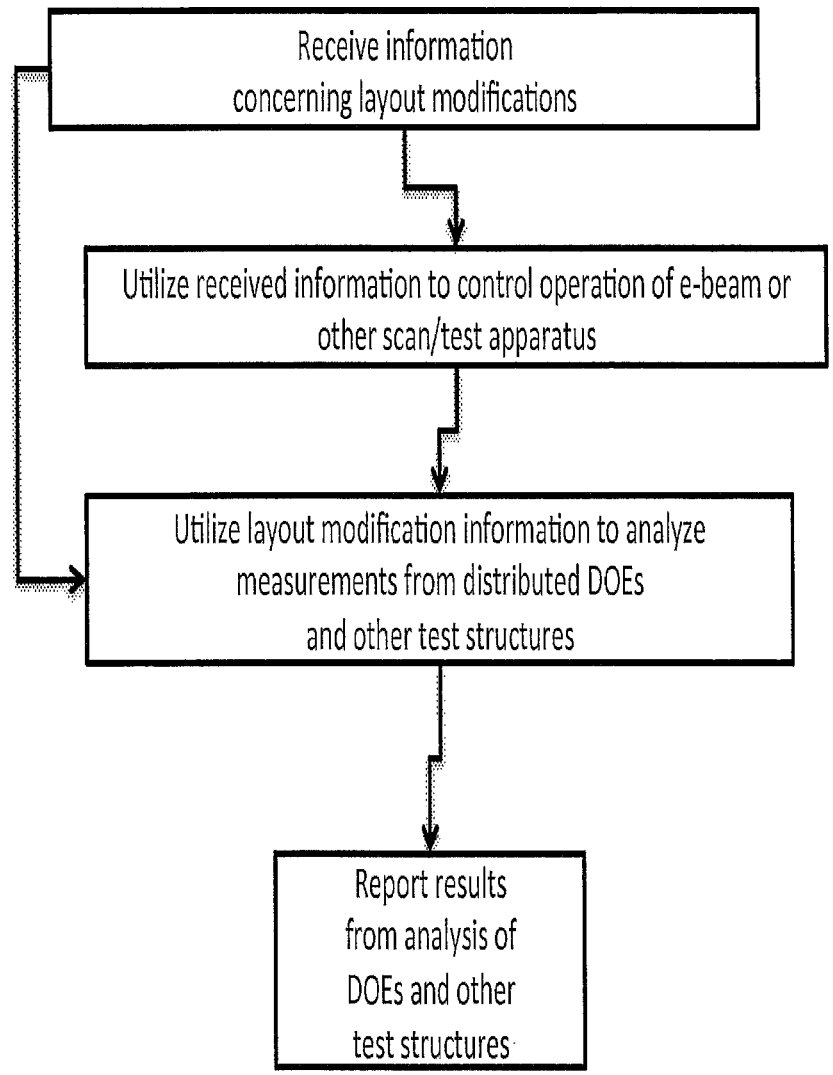
FIG. 8 depicts an exemplary process flow for utilizing the opportunistically inserted test structures (as per FIG. 7 or 10) to generate useful results.
Figure 9:
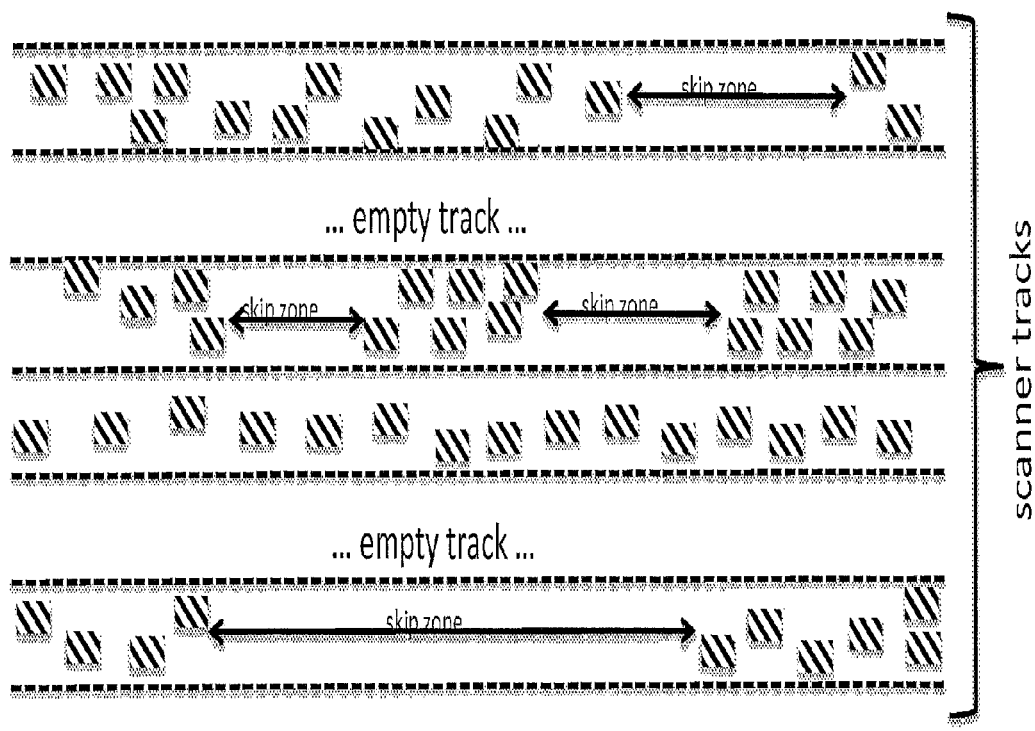
FIG. 9 conceptually depicts a portion of an exemplary wafer or die, showing the opportunistically inserted test pads and/or structures arranged to produce empty track(s) and/or skip zone(s) that enable faster e-beam scanning.
Figure 10:
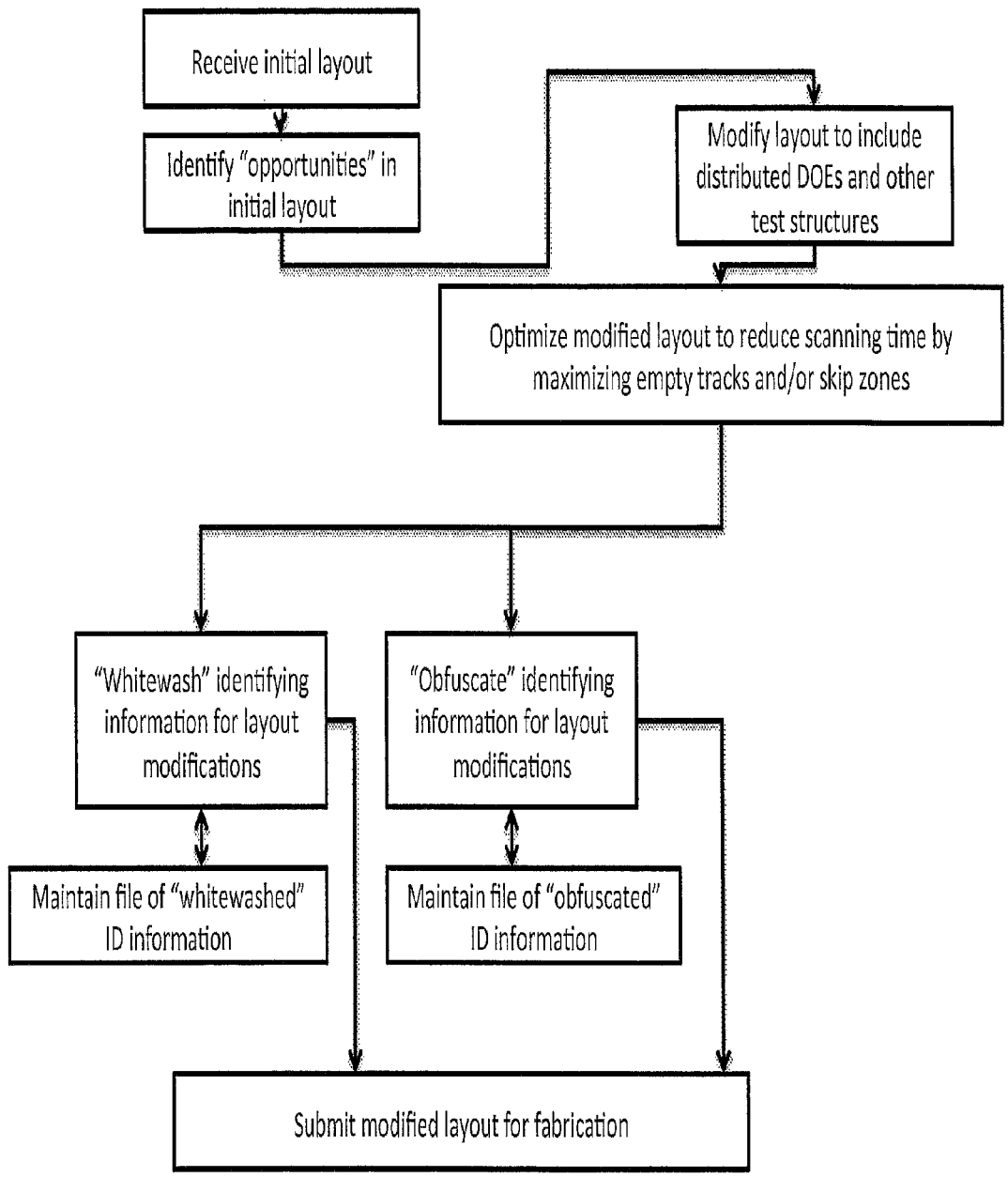
FIG. 10 depicts an alternative exemplary process flow for opportunistic test structure insertion in accordance with certain embodiments of the invention.

FIG. 6 depicts an exemplary layout in accordance with the invention, in which the filler cells (F), tap cells (T), decap cells (dC), and dummy fill (diagonally hashed) regions of the FIG. 5 layout are replaced by self-contained test structures (TS, dC-T, and dotted region, respectively).

As persons skilled in the art will recognize, numerous options exist for the selection of particular test structures to be opportunistically instantiated in accordance with the present invention.

Product ICs in accordance with the invention may include test structures adapted for in-line systematic defect inspection, by bright field and/or e-beam (or other charging), of product layout patterns most susceptible to systematic defects, including multi-patterning structures. Such test structures preferably include canary structures (i.e., sub-design rule structures used to explore process-layout marginalities).

Product ICs in accordance with the invention may also include test structures adapted for in-line random defect inspection, by bright field and e-beam tools, of product-like patterns for the most likely defects, such as single line opens and most likely via open locations (including canary structures).

Product ICs in accordance with the invention may also include test structures adapted for in-line metrology, such as structures to extract overlay/misalignment, product-specific patterns for poly CD, MOL CD, via bottom CD, metal CD and height, dielectric heights, etc., and may be testable electrically and/or by Scanning Electron Microscope (e.g., for overlay, line CD and profile).

Product ICs in accordance with the invention may also include Physical Failure Analysis (PFA) structures for likely systematic defects, where such PFAs may include product specific layout patterns (including canary structures) and pads for probing.

And product ICs in accordance with the invention may also include any combination of the above-noted, or other, usable test structures.

For test-enabled decap cells, the preferred test structures are M1 structures for Single Line Open inspection.

Important goals for the design of test structures in accordance with certain embodiments of the invention are that: (1) test structures should not affect printability of the active geometry (i.e., standard cells or interconnect), and/or (2) test structures should be representative of the active cell properties (printability and electrical characteristics).

Figure 11:
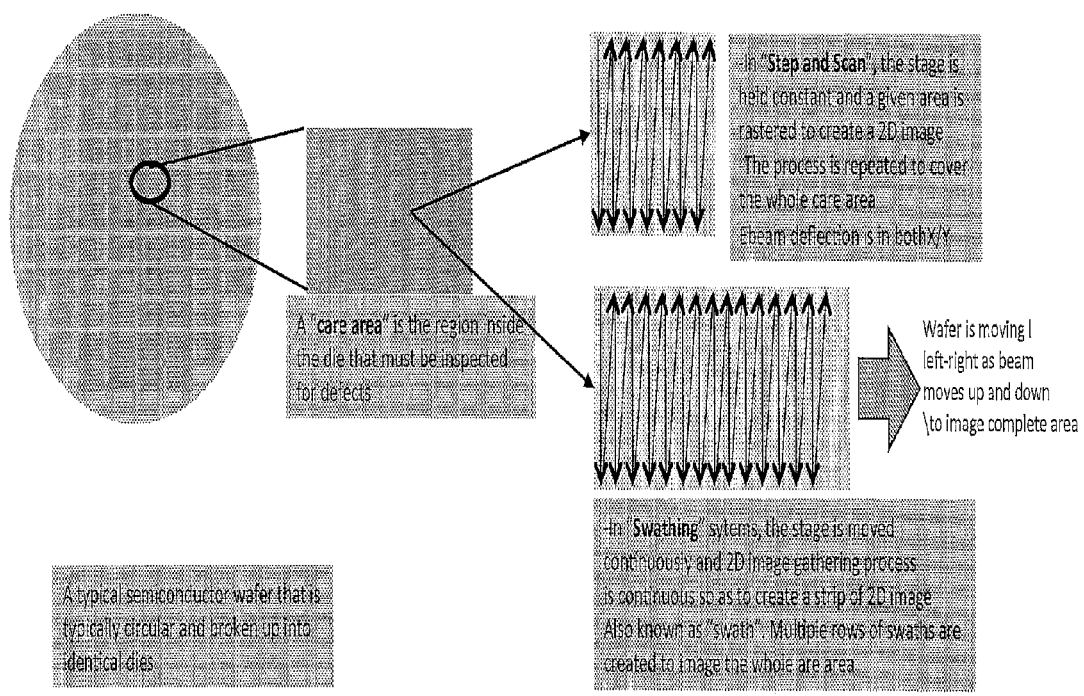
FIG. 11 depicts the prior-art "step and scan" and "swathing" techniques.

FIG. 11 depicts the prior-art "step and scan" and "swathing" techniques.

Figure 12:
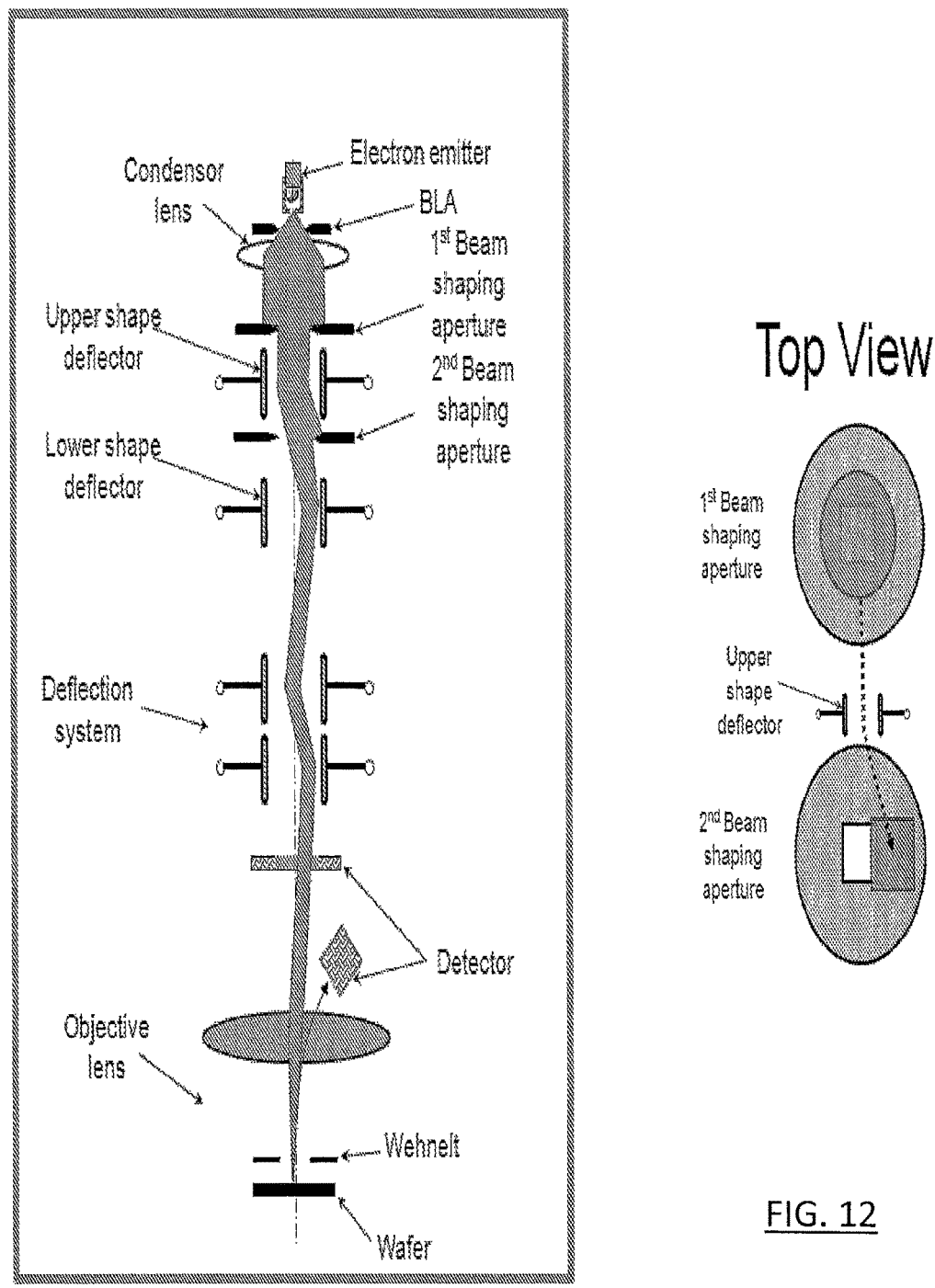
FIG. 12 depicts a beam scanning/shaping apparatus according to various embodiments of the invention.

FIG. 12 depicts a beam scanning/shaping apparatus according to the invention.

Figure 13:
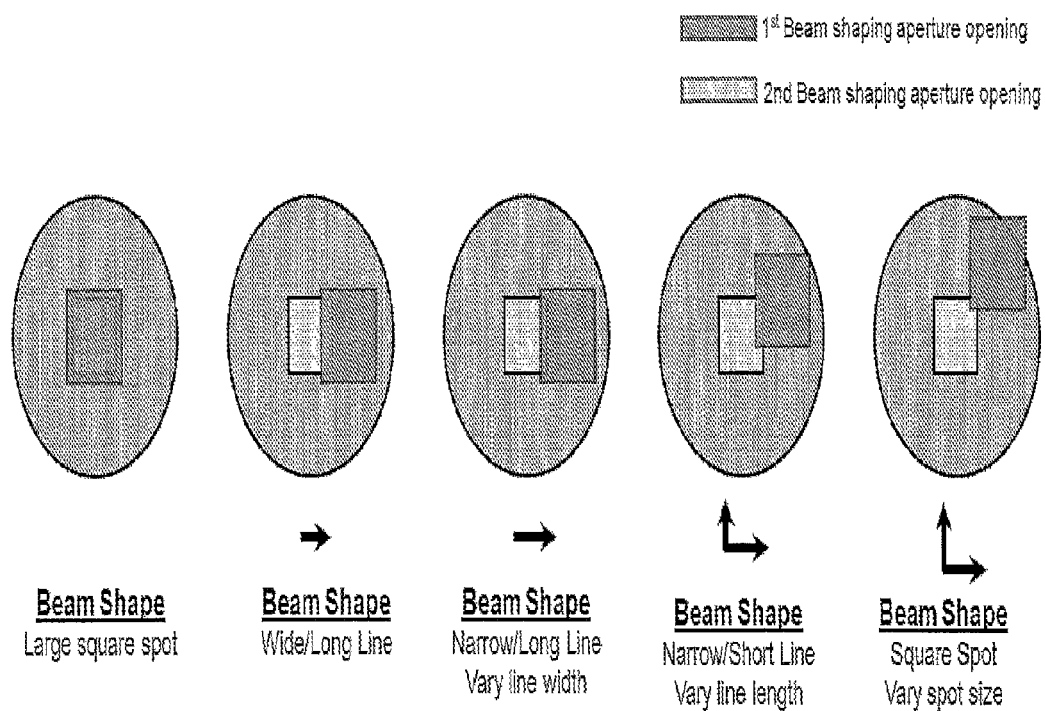
FIG. 13 shows examples of the beam shapes that can be realized using the column of FIG. 12.

FIG. 13 shows examples of the beam shapes that can be realized using the column of FIG. 12.

Figure 14:
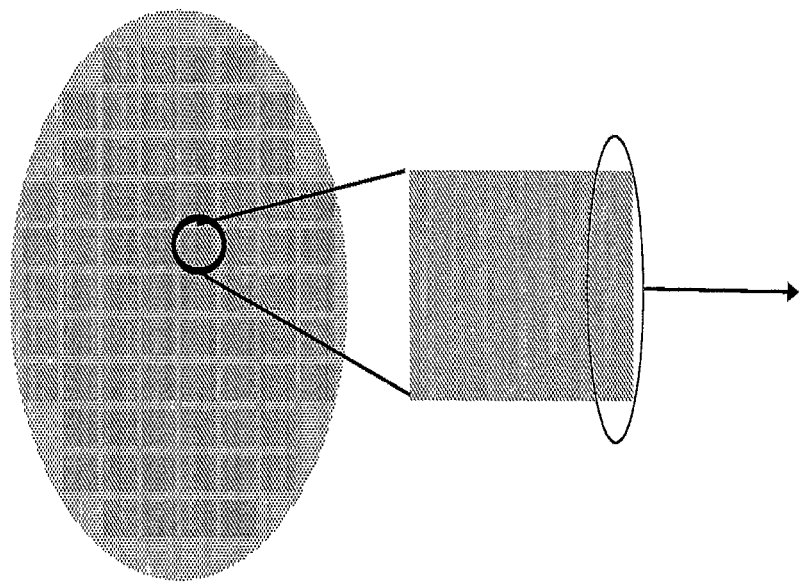
FIG. 14 depicts an exemplary semiconductor wafer that is typically circular and broken up into identical dies, and further depicts an example case where all of the test structures are located in the scribe areas of the die.

FIG. 14 depicts an exemplary semiconductor wafer that is typically circular and broken up into identical dies, and further depicts an example case where all of the test structures are located in the scribe areas of the die.

Figure 15:
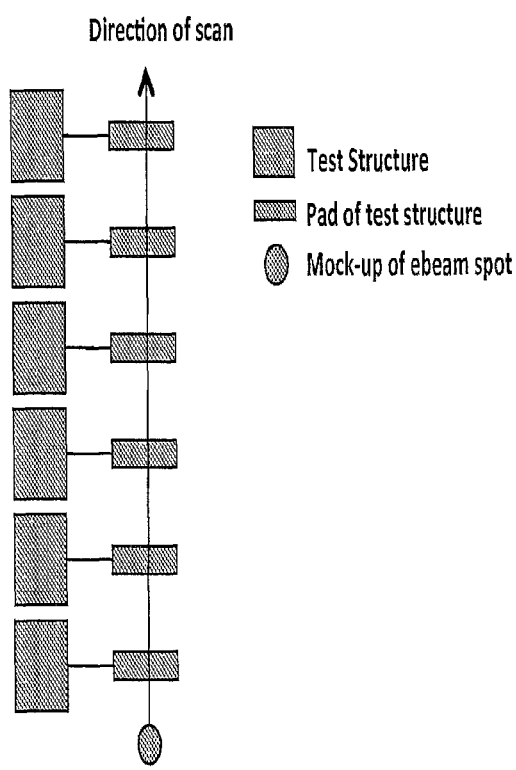
FIG. 15 illustrates a series of test structures laid out with their pads in a column, where a spot of the electron beam scans over the pads by the relative motion of the wafer to the spot.

FIG. 15 illustrates a series of test structures laid out with their pads in a column, where a spot of the electron beam scans over the pads by the relative motion of the wafer to the spot.

Figure 16:
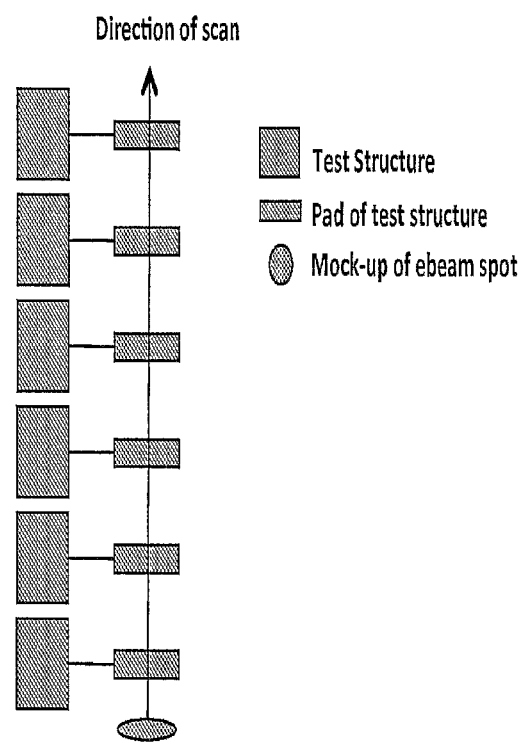
FIG. 16 shows an illustration of an electron spot shaped in a non-circular manner to match the size and shape of the pad, so as to maximize the electron current that is delivered to the pad.

FIG. 16 shows an illustration of an electron spot shaped in a non-circular manner to match the size and shape of the pad, so as to maximize the electron current that is delivered to the pad.

Figure 17:
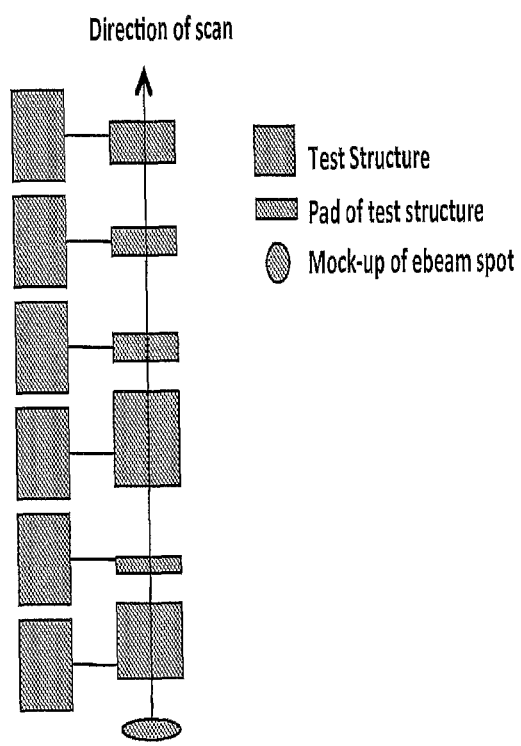
FIG. 17 shows an illustration of pad shapes being sized according to the amount of charge that needs to be delivered to the test structures, wherein test structures needing more charge have longer pads along the scanning direction of the beam to increase the beam dwell time on the pad.

FIG. 17 shows another illustration of pad shapes being sized according to the amount of charge that needs to be delivered to the test structures, wherein test structures needing more charge have longer pads along the scanning direction of the beam to increase the beam dwell time on the pad.

Figure 18:
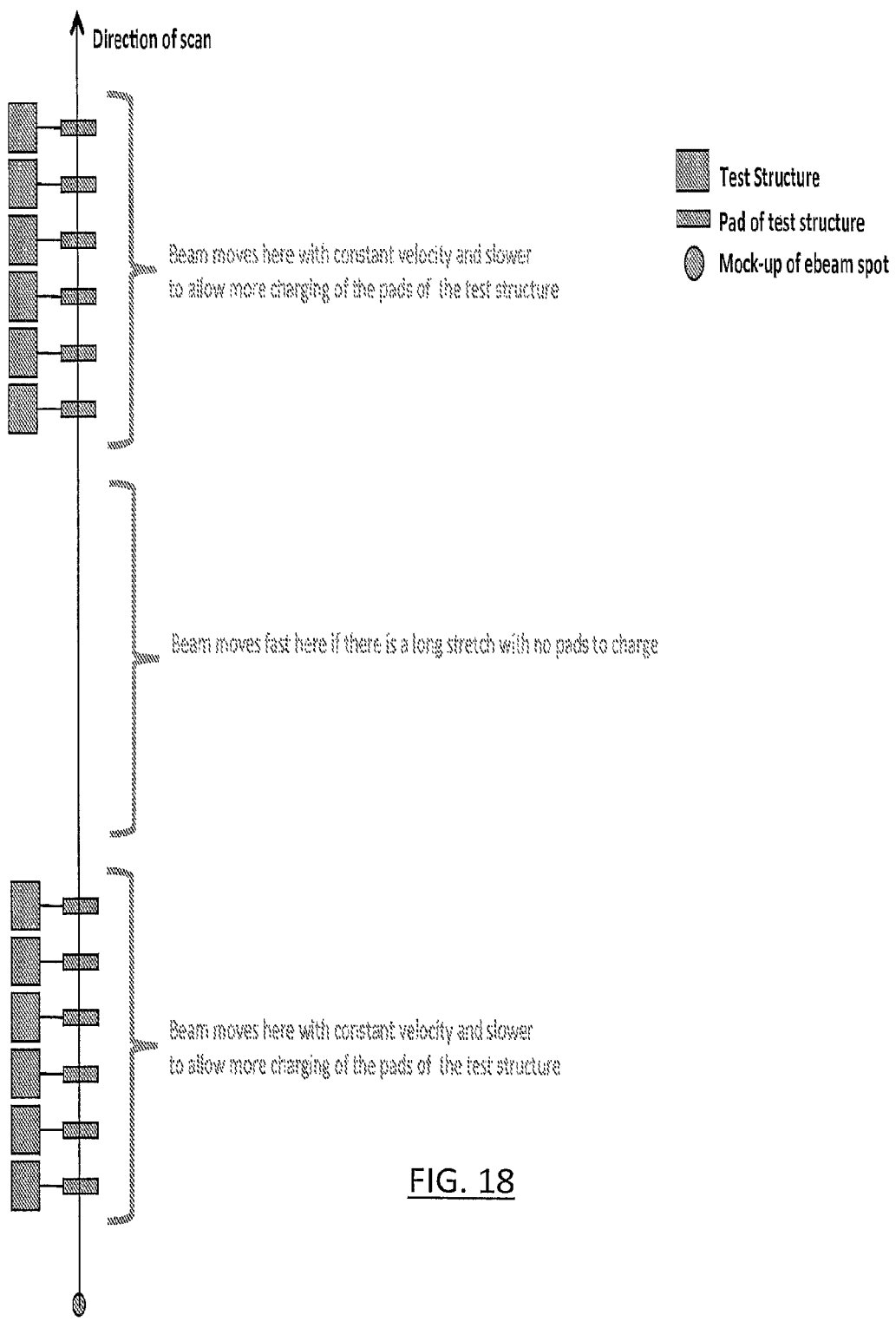
FIG. 18 depicts a scenario in which the beam moves fast if there is a long stretch with no pads to charge, but with constant velocity and slower in populated regions to allow more charging of the pads of the test structures.

FIG. 18 depicts a scenario in which the beam moves fast if there is a long stretch with no pads to charge, but with constant velocity and slower in populated regions to allow more charging of the pads of the test structures.

Figure 19:
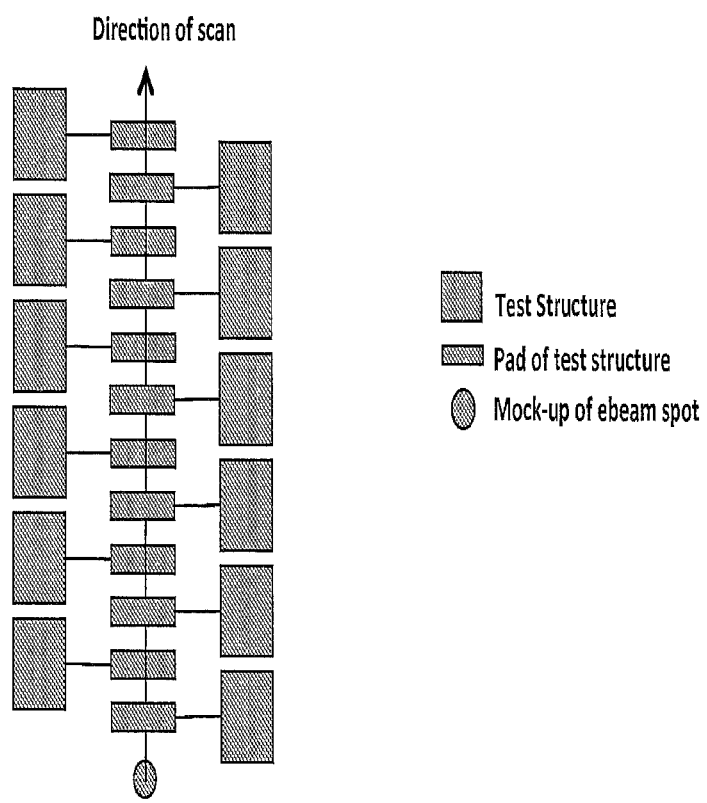
FIG. 19 shows test structures laid out on either sides of the pads, which allows a larger number of test structures to be scanned with a single pass of the beam on the wafer.

FIG. 19 shows test structures laid out on either sides of the pads, which allows a larger number of test structures to be scanned with a single pass of the beam on the wafer.

Figure 20:
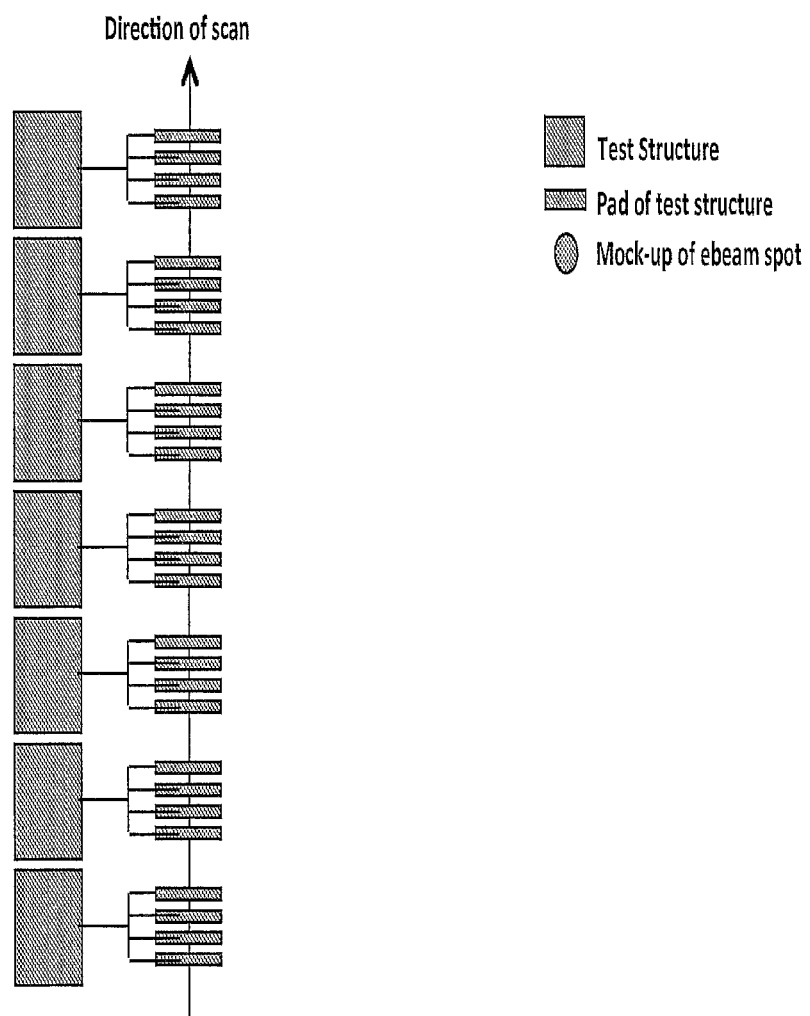
FIG. 20 shows how solid pads may be split into finer lines or alternate shapes so that their layout will be compatible with the design rules of the semiconductor process.
Figure 21:
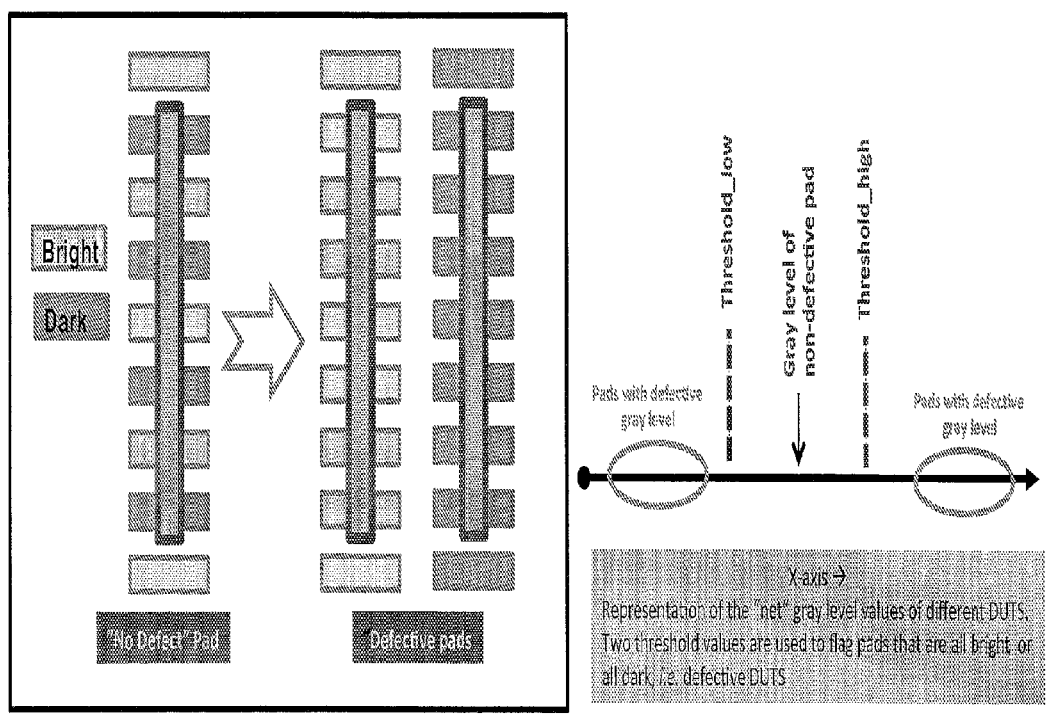
FIG. 21 depicts "net grey" pads for use with certain embodiments of the invention.

FIG. 20 shows how solid pads may be split into finer lines or alternate shapes so that their layout will be compatible with the design rules of the semiconductor process. Reference is now made to FIG. 21, which depicts a VC DUT with size and shape to accommodate non-circular incident e-beams for readout in a single spot measurement, with a pad group designed with only alternating lines connected the DUT, and the remaining lines of pad connected to floating or ground such that their polarity is opposite to that of the functioning DUT.

For a functioning DUT, the pad lines will appear as alternating bright/dark, whereas for a non-functioning DUT (i.e. one that has failed), pads are all bright or all dark. The advantage here is that the "net" gray level for all non-defective DUTs is effectively always the same, and the image computer can use the same thresholds for the detection of all defective DUTs. This simplifies the software algorithm and the hardware of the image computer.

Figure 22:
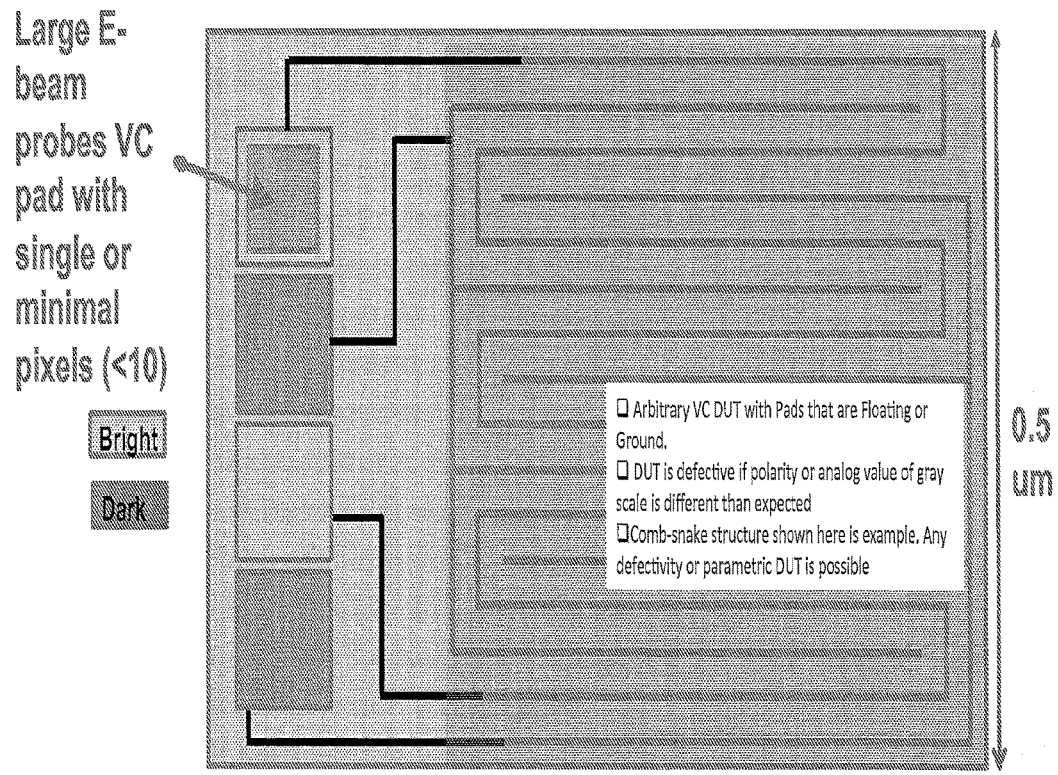
FIG. 22 conceptually illustrates one embodiment of a VC DUT in accordance with certain aspects/embodiments of the invention.

Reference is now made to FIG. 22, which conceptually illustrates one embodiment of a VC DUT in accordance with certain aspects of the invention. Pads are read off by using a large spot size e-beam tool, either by a single pixel measurement (i.e., single analog readout) or N analog values at same location (i.e., N-sample digital-averaging could be used to improve SNR).

The beam and pad are designed to have more or less the same footprint. In this case, the X/Y aspect ratio −1. Beam is square shaped to match the pad, but could also be circular with similar size. Pictograph shows four pads, but the invention applies to one or multiple pads equivalently.

Figure 23:
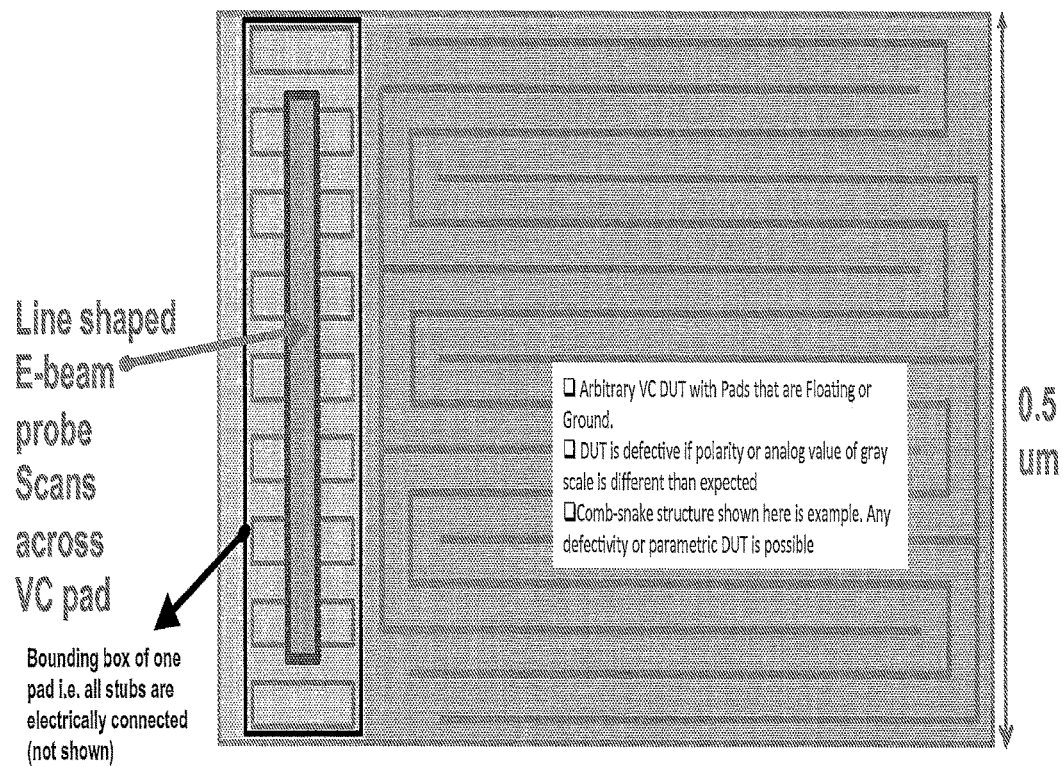
FIG. 23 conceptually illustrates another embodiment of a VC DUT in accordance with certain aspects/embodiments of the invention; and, FIG. 24 conceptually illustrates another embodiment of a VC DUT in accordance with certain aspects/embodiments of the invention.

Reference is now made to FIG. 23, which conceptually illustrates another embodiment of a VC DUT in accordance with certain aspects of the invention. Pads are read off by using a large spot size e-beam tool, either by a single pixel measurement (i.e., single analog readout) or N analog values at same location (i.e., N-sample digital-averaging could be used to improve SNR). Overall, pad and beam have similar footprint on wafer. However, to accommodate a non-symmetric beam (X/Y aspect ratio >3) while meeting semiconductor layout design rules, the pad is split into array of narrow horizontal lines. Pictograph shows one pad, but the invention applies to one or multiple pads equivalently.

Figure 24:
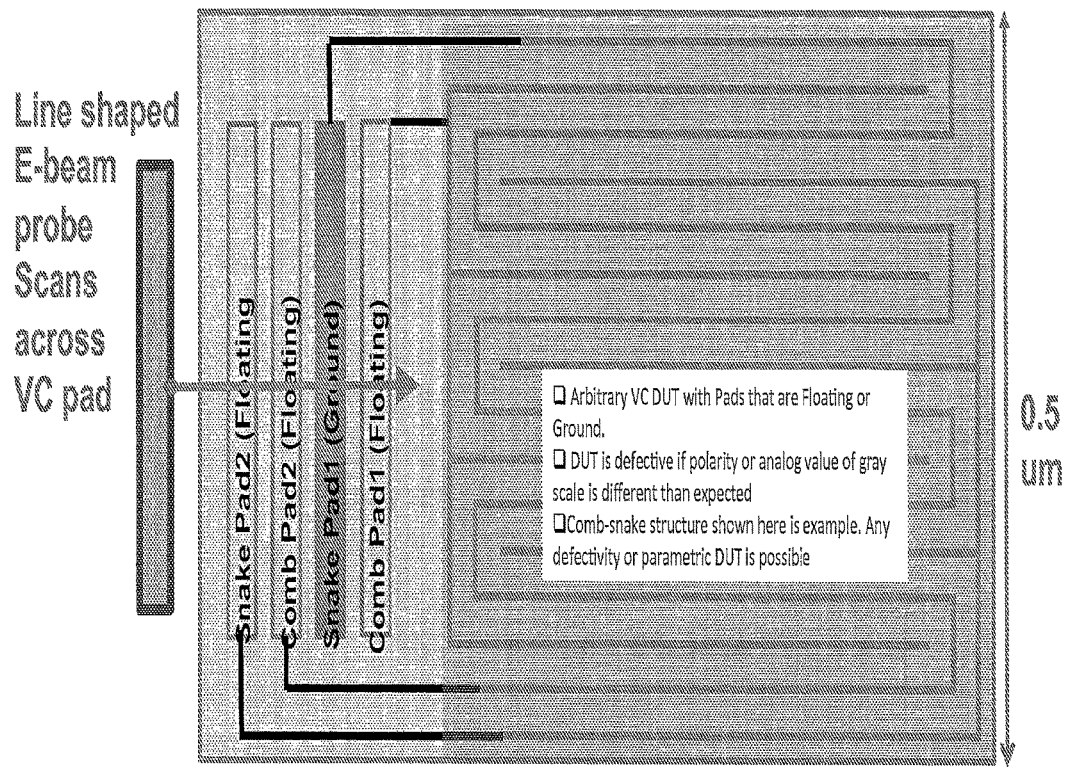

Reference is now made to FIG. 24, which conceptually illustrates another embodiment of a VC DUT in accordance with certain aspects of the invention. Pads are optimized for line-shaped beam. X/Y Aspect ratio of pads and beam is greater than 3. Pads are read off like a bar-code scanner, with the polarity of each pad being read off in fewer than 10 pixels. Pictograph shows four pads, but the invention applies to one or multiple pads equivalently.

Although the present invention has been particularly described with reference to embodiments thereof, it should be readily apparent to those of ordinary skill in the art that various changes, modifications and substitutes are intended within the form and details thereof, without departing from the spirit and scope of the invention. Accordingly, it will be appreciated that in numerous instances some features of the invention will be employed without a corresponding use of other features. Further, those skilled in the art will understand that variations can be made in the number and arrangement of components illustrated in the above figures.

What we claim in this application is:

1. An apparatus for detecting defects in an integrated circuit, wherein the integrated circuit includes a plurality of predetermined locations each having a predetermined surface area and a major axis and the apparatus comprising:

a target holder for holding said integrated circuit; an e-beam source that directs an e-beam toward each of the plurality of predetermined locations on the integrated circuit;

a focusing column that accelerates the e-beam and separately, for each of the plurality of predetermined locations, focuses the e-beam to a predetermined narrow non-circular spot that is within the predetermined surface area of each of the plurality of predetermined locations based upon the major axis, the focusing column including a condensor lens, an objective lens and a Wehnelt, wherein the condensor lens and the objective lens are disposed between the e-beam source and the Wehnelt, and wherein the Wehnelt is disposed in a location of the focusing column that receives the e-beam and the secondary electrons; and a detector that detects a voltage contrast image of secondary electrons emitted from the integrated circuit after the e-beam strikes each of the plurality of predetermined locations of the integrated circuit.

2. The apparatus as defined in claim 1, further including a computer into which is input the image and which determines whether a defect exists within the integrated circuit based upon the voltage contrast image, thereby forming an inspection tool.

3. The apparatus as defined in claim 1 wherein the detector is disposed within the focusing column, and containing an opening through which the electron beam from the electron source passes therethrough.

4. The apparatus as defined in claim 3, wherein the focusing column selectively focuses the e-beam to predetermined locations of e-beam target pads, at least certain ones of said e-beam target pads having an asymmetric aspect ratio.

5. The apparatus as defined in claim 4, wherein only a single pixel measurement is obtained as a voltage contrast measurement from each e-beam target pad.

6. The apparatus as defined in claim 5, wherein the focusing column selectively focuses the e-beam using an e-beam spot with an elongated major axis.

7. An apparatus, as defined in claim 6, wherein the elongated major axis of the e-beam spot is matched in dimension to that of the targeted e-beam pads, so as to maximize scanning efficiency.

8. An apparatus, as defined in claim 6, wherein the elongated major axis of the e-beam spot is matched in a first dimension to that of the targeted e-beam pads, and wherein an elongated minor axis of the e-beam spot perpendicular to the elongated major axis is matched in a second dimension to that of the targeted e-beam pads.

9. An apparatus, as defined in claim 6, wherein each of the targeted e-beam pads is positioned along a linear scan line, and wherein the elongated major axis of the e-beam spot is oriented perpendicular to the scan line.

10. An apparatus, as defined in claim 6, wherein the predetermined narrow non-circular spot of the e-beam is substantially rectangular.

11. An apparatus, as defined in claim 10, wherein the predetermined narrow non-circular spot of the e-beam is square.

12. An apparatus for detecting defects in an integrated circuit, wherein the integrated circuit includes a plurality of predetermined locations and the apparatus comprising:
  a target holder for holding said integrated circuit; an e-beam source that directs an e-beam toward each of the plurality of predetermined locations on the integrated circuit;
  a focusing column that accelerates the e-beam of electrons and focuses the e-beam to each of the plurality of predetermined locations, the focusing column including a condensor lens, an objective lens and a Wehnelt; and
  a detector that obtains e-beam excited measurements, without continuously scanning, from the plurality of locations by selectively sampling fewer than ten pixels from an e-beam pad associated with each of said plurality of locations.

13. The apparatus as defined in claim 12, wherein the focusing column selectively focuses the e-beam of electrons to e-beam target pads, at least certain ones of said e-beam target pads having an asymmetric aspect ratio.

14. The apparatus as defined in claim 12, wherein only a single pixel measurement is obtained as a voltage contrast measurement from each e-beam target pad.

15. An apparatus, as defined in claim 12, wherein the focusing column selectively focuses the e-beam using an e-beam spot with an elongated major axis.

16. An apparatus, as defined in claim 15, wherein the elongated major axis of the e-beam spot is matched in dimension to that of the targeted e-beam pads, so as to maximize scanning efficiency.

17. An apparatus, as defined in claim 15, wherein the elongated major axis of the e-beam spot is matched in a first dimension to that of the targeted e-beam pads, and wherein an elongated minor axis of the e-beam spot perpendicular to the elongated major axis is matched in a second dimension to that of the targeted e-beam pads.

18. An apparatus, as defined in claim 15, wherein each of the targeted e-beam pads is positioned along a linear scan line, and wherein the elongated major axis of the e-beam spot is oriented perpendicular to the scan line.

19. An apparatus for detecting defects in an integrated circuit, wherein the integrated circuit includes a plurality of predetermined locations and the apparatus comprising:
  a target holder for holding said integrated circuit; an e-beam source that directs an e-beam of electrons toward each of the plurality of predetermined locations on the integrated circuit;
  a focusing column that accelerates the e-beam of electrons and focuses the e-beam to each of the plurality of predetermined locations, the predetermined locations having a plurality of e-beam skip zones there between, thereby allowing the focusing column to skip at least 10% of its overall scan length, the focusing column including a condensor lens, an objective lens and a Wehnelt; and
  a detector that obtains e-beam excited measurements, without continuously scanning, from the plurality of locations from an e-beam pad associated with each of said plurality of locations.

20. The apparatus according to claim 19 wherein the focusing column further skips one or more empty e-beam scanning tracks, each empty e-beam scanning track spanning an entire width of the area of functional product circuitry.

21. The apparatus according to claim 19 wherein the focusing column further skips at least 20% of its overall scan length.

* * * * *